United States Patent [19]

Miller, Jr. et al.

[11] 4,199,323

[45] Apr. 22, 1980

[54] ANALYTICAL TECHNIQUE FOR QUANTITATING ACID/SALT AND BASE/SALT SAMPLES FOR SPECIES CONCENTRATION

[75] Inventors: Theodore E. Miller, Jr.; Timothy S. Stevens, both of Midland, Mich.

[73] Assignee: The Dow Chemical Company, Midland, Mich.

[21] Appl. No.: 913,786

[22] Filed: Jun. 8, 1978

[51] Int. Cl.² ............ G01N 31/04; G01N 27/08
[52] U.S. Cl. ............ 23/230 R; 73/61.1 C; 210/24; 210/25; 210/31 C; 210/198 C; 422/70
[58] Field of Search ........... 23/230 R; 73/61.1 C; 210/24, 25, 31 C, 198 C; 422/70

[56] References Cited

U.S. PATENT DOCUMENTS

| | | | |
|---|---|---|---|
| 2,617,766 | 11/1952 | Emmett et al. | 210/25 |
| 2,920,398 | 11/1975 | Small et al. | 23/230 R |
| 3,607,083 | 9/1971 | Chowdhry | 23/230 R |
| 3,897,213 | 7/1975 | Stevens et al. | 210/25 |
| 3,915,642 | 10/1975 | Small et al. | 23/230 R |
| 3,918,906 | 11/1975 | Small et al. | 23/230 R |
| 3,920,397 | 11/1975 | Small et al. | 23/230 R |
| 3,923,460 | 12/1975 | Parrott et al. | 23/230 R |
| 3,925,019 | 12/1975 | Small et al. | 23/230 R |
| 3,926,559 | 12/1975 | Stevens | 23/230 R |

Primary Examiner—Michael S. Marcus

[57] ABSTRACT

Acid or alternately base species concentration in aqueous and non-aqueous samples is quantitated, in the presence of interfering ionic salts, using most preferably differential conductivity detection combined with ion-exchange derivatization, wherein characteristically the acid or base species is derivatized to water, and blended indistinguishably in a required aqueous carrier phase, and the interfering salt(s) is derivatized to a distinguishable hydroxide or acid derivative(s). Using the preferred mode of detector read-out, the calibrated peak of the conductimetric response of the salt derivative(s) is compared to the peak of the conductimetric response of the sample and the response differential is displayed and used to predict the acid or base species concentration. The salt(s) concentration (with some exceptions) may be simultaneously predicted since it is proportional to the first mentioned peak. The technique has utility with respect to acids and bases broadly, and most advantageously is used with respect to strong and moderately strong acids and bases of a $pK_a$ and $pK_b$ value, respectively, of about 2 or less.

28 Claims, 5 Drawing Figures

ANALYTICAL TECHNIQUE FOR QUANTITATING ACID/SALT AND BASE/SALT SAMPLES FOR SPECIES CONCENTRATION

FIELD OF THE INVENTION

The invention relates generally to an improved analytical technique and instrument for assaying aqueous and non-aqueous samples for salt, base and acid species concentration. More particularly, the invention relates to a select ion-exchange derivatization technique which is particularly useful for determining acid and base species concentration in the presence of salt interferences such as typically encountered in on-line or on-site analysis of acid or caustic scrubbers, chlor-alkali cell effluents, and the like, as illustrative examples.

BACKGROUND OF THE INVENTION

Differential conductivity methods for carrying out analytical determinations are known as exemplified by U.S. Pat. Nos. 3,607,083 and 3,950,137. These methods depend typically on the addition of reagents to precipitate interfering ions. As such, the methods tend to be useful for only a relatively few species. Accumulation of the precipitate also produces messy instrument clean-up and fouling problems. Thus, the technique is generally little favored where alternate methods are available, and particularly so for on-line automated, and thus substantially unattended, analysis systems.

Known ion-exchange chromatographic analytical techniques are also pertinent to the inventive subject matter since the chemical reactions performed may be similar to that practiced by the invention. The prior art is represented by the teachings of U.S. Pat. No. 3,920,397. The invention is distinguished from the referenced ion-exchanged chromatographic technique since the latter is designed using basic or acidic carrier phases selected on the criteria of suitability to separate certain defined ion species, the carrier being ultimately converted to water. Hence, the conversion of the species of interest to water is not followed or predisposed by this technique. In addition, the technique is unsuitable for assaying acid and base samples directly, and is designed rather for detecting and quantitating chromatographically separated cation and anion species.

What the art refers to as total ionic content analyzers and single ion analyzers also relate to the invention since the techniques employ conductimetric detectors, in conjunction with ion-exchange derivatization steps. Examples of this prior art are published in U.S. Pat. Nos. 3,897,213, 3,915,642 and 3,918,906. These methods are generally characterized by the conversion of a mixture of ionic species to a single, preselected species. The step is used to maximize the accuracy of a conductimetric measurement. The invention is thus distinguished over these quite different methods neither designed or suitable for the quantitative analysis of acid and base species in acid/salt and base/salt sample matrices.

Titration of strong acid and base solutions is also considered pertinent prior art from a comparative standpoint. Thus, current industrial process stream monitoring techniques often favor automatic titration analysis for strong and moderately strong base and acid determinations. However, automated titration instrumentation is expensive and tends to require a laborious maintenance schedule. Thus, there is a need to develop a simpler, more reliable instrument and technique for the quantitative analysis of acid and base samples which contain interfering salt(s).

GENERAL DISCLOSURE OF THE INVENTION

The invention is practiced based on a principle of derivatizing the acid or base species of interest to water which is indistinguishably blended into the background of a required aqueous based eluent or carrier phase. In conjunction with this reaction, the interfering salt(s) is simultaneously converted to a detectable acid or hydroxide derivative(s). Unless otherwise indicated, the terms "acid" and "base" whenever used herein denotes species with a $pK_a$ and $pK_b$ of about 13 or less. Preferred applications are taught with respect to strong and moderately strong acids and bases of a $pK_a$ and $pK_b$ of about 2 or less.

The ion-exchange derivatization reactions, supra, are preferably carried out in a strong base form ion-exchange means in the hydroxide ion form for quantitating acid species, and conversely, a strong acid form ion-exchange means, in the hydrogen (hydronium) ion form is preferably employed for base species. In the first mentioned mode, i.e., the determination of acid species, essentially all anions are stripped from the sample and captured at the active ion-exchange sites. The ion-exchange means gives up to the sample an equivalent proportion of $OH^-$ ions, whereby the acid is derivatized to water, and the salt(s) to a hydroxide(s) which is distinguished by the salt cations present in the sample. The mode for quantitating an aqueous base species relies on the similar principle of stripping the sample of essentially all cations, and returning to the sample an equivalent proportion of hydrogen ions. Hence, the base is derivatized to water (indistinguishable or essentially so in the carrier phase) and the salt(s) to an acid derivative(s) distinguished by the salt anion(s) present. Since the system advantageously uses batch sampling and preferred deionized water as the carrier, long column life is assured.

In respect to the preferred detector system, dual conductivity cells of the flow-through design are preferably used to determine the conductimetric response of the sample and ion-exchange effluent, i.e., salt derivative, respectively. With double pass through techniques a single cell can be suitably employed in an equivalent mode. A diffuser column or static mixer is also most preferably employed to produce a gaussion or skewed gaussion distribution and dilution of the sample in the carrier. Employment of the diffuser column is desirable since response linearity is improved at the resulting lower sample ion concentrations. Peak picker circuits are preferably utilized to compare the calibrated responses of the conductivity cells, using the criteria of the differential in peak height to estimate or predict base or acid concentration. Alternatively, the peaks may be integrated and compared, and the difference in the calibrated peak area (as opposed to peak height) used to quantitate the acid or base species concentration. The salt concentration may be simultaneously determined since it is proportional to the effluent peak (provided the salt mixture remains known and thus calibratable).

Also under the special conditions where only the salt concentration is of interest, in an acid/salt or base/salt matrix, the first detection step as well as the preferred requirement of a diffuser column may be omitted from the technique. In such practices, the base or acid species is treated as the interfering ions, which interference is effectively eliminated by converting the base or acid, as applies, to the carrier form. Consequently, the response of only the ion-exchange effluent may be suitably employed to detect and quantitate the desired salt species concentration.

As alternate forms of the invention, the concentration of the sample and effluent may be determined by modified detector systems. Alternate detector forms particularly contemplated, and which may be set up to operate using the differential response principle described in detail above, would desirably include flow-through polarographic cells, differential refractometers, ion specific electrodes, spectrophotometers, and detectors generally capable of detecting and quantifying the species of interest.

The preferred differential conductimetric detection mode is ideally suited for use in applications generally described by the condition wherein the acid/base and salt mixture is about 90% or more dissociated ionically in the diluted sample/eluent stream at the critical point of the first detection step (and referring specifically to the ionic dissociation in the area of maximum sample concentration).

Where the condition is not inherently obeyed, or otherwise acceptably achieved such as by ionic dissociation maximizing steps, or by upgrading the species of interest to a stronger acid or base (such as by substituting a suitable inorganic ion-exchange column for the diffuser column), special case exemptions should nevertheless be recognized and considered extendable to the preferred conductimetric detection mode. Thus, depending on the accuracy required, the 90% ionic dissociation limit is not necessarily truly extendable to cases such as where minor salt interferences appear, or to the case where it may be necessary to calibrate only over a relatively narrow range. Where the latter applies, frequently acceptable accuracy may thus be achieved by calibrating the sample mixture over the narrower range of interest. Alternately, non-ionization dependent detection systems such as those noted above and other known systems, may be most advantageously selected either to maximize accuracy or extend the applicability of the technique to generally all acid and base species.

The preferred instrumentation for practicing the invention is shown in the drawing wherein.

DETAILED DESCRIPTION OF THE INVENTION

Figure 1:
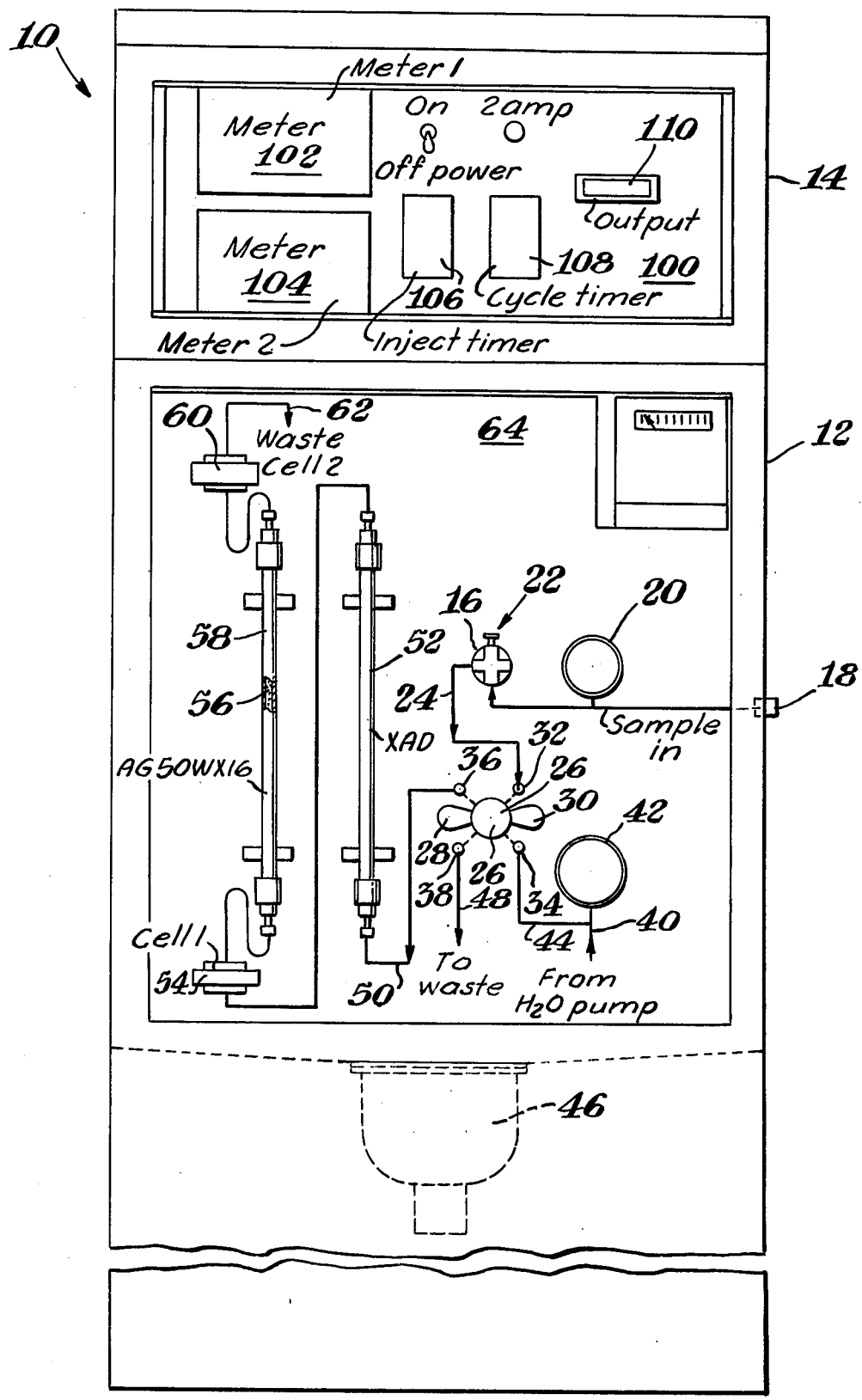
FIG. 1 is an elevation view of an analytical instrument constructed according to the principles of the invention.

A preferred and illustrative form of the invention is embodied in an instrument 10, shown in FIG. 1, and comprising sealed cabinets 12, 14. The lower cabinet 12 contains a 3-way manual selector valve 16 (preferably a product code No. 201-54 slider valve from Altex Corp.). A sample entry line and fitting 18 admits a sample stream to valve 16 and a line pressure gauge 20.

The selector valve includes an auxiliary port 22 for manually admitting standards by the syringe loading technique. The manual valve selects and routes the sample stream or the manually injected standard through an outlead line 24 to a pneumatic double acting automatic sample injection valve 26 defining a carrier loop 28 and a sampling loop 30. Injection valve 26 (preferably an Altex Code No. 201-56 valve with Altex Code No. 201-12 pneumatic actuators) is equipped with a sample inlet 32, a carrier inlet 34, a sample/carrier outlet 36, and a sample purge outlet 38. An eluent or carrier stream is admitted continuously to carrier inlet 34 via a metering pump 40 (preferably a Milton Roy Simplex Mini-pump, Model No. 396-31), a line pressure gauge 42, and a carrier inlet line 44 (see also FIG. 2). The eluent is routed through carrier loop 28 to the sample/carrier outlet. Sample is routed through sampling loop 30 to sample purge outlet 38, or alternately, a loop-captured sample aliquot is flushed from the sample/carrier outlet 36, depending on the valving position. The purge outlet communicates through an outlead line 48 with a waste sump 46. The sample/carrier outlet communicates through a second outlead line 50 with a resin packed diffuser column or static mixer 52. The diffuser column communicates progressively with a flow-through conductivity cell 54, ion-exchange derivatization beads or means 56, packed in a glass column 58, and a second flow-through conductivity cell 60. Ultimately, the spent sample is disposed of to waste sump 46 through an outlead line 62.

Preferred strong acid form ion-exchange means, in the hydrogen ion form, and useful for analyzing base species, are the commercially trade designated AG50WX16 resin, from Bio-Rad Lab., Richmond, Calif., also Amberlite ® IR-120 resin from Rohm & Haas, and also Dowex ® type 50WX16 resin from the Dow Chemical Company (all 200–400 standard U.S. mesh, sulfonated cross-linked divinyl benzene strongly acidic cation exchange resins). Preferred strong base form ion-exchange means in the hydroxide ion form for quantitating aqueous acid species are the trade designated AG1X10 from Bio-Rad, Amberlite IRA-400 and Dowex ® 1-X10, (all 200–400 standard U.S. mesh aminated cross-linked divinyl benzene strongly basic anion exchange resins requiring conversion to the hydroxide form by washing in caustic according to the known technique). The commerical ion-exchange resins, supra, are described and characterized in further detail in the publication "Materials, Equipment and Systems for Chromatography Electrophoresis Immunochemistry and Membrane Filtration", Bio-Rad Lab., Price List C, (March 1977), pp. 6–15, this publication being hereby incorporated in the present teaching by reference.

Figure 2:
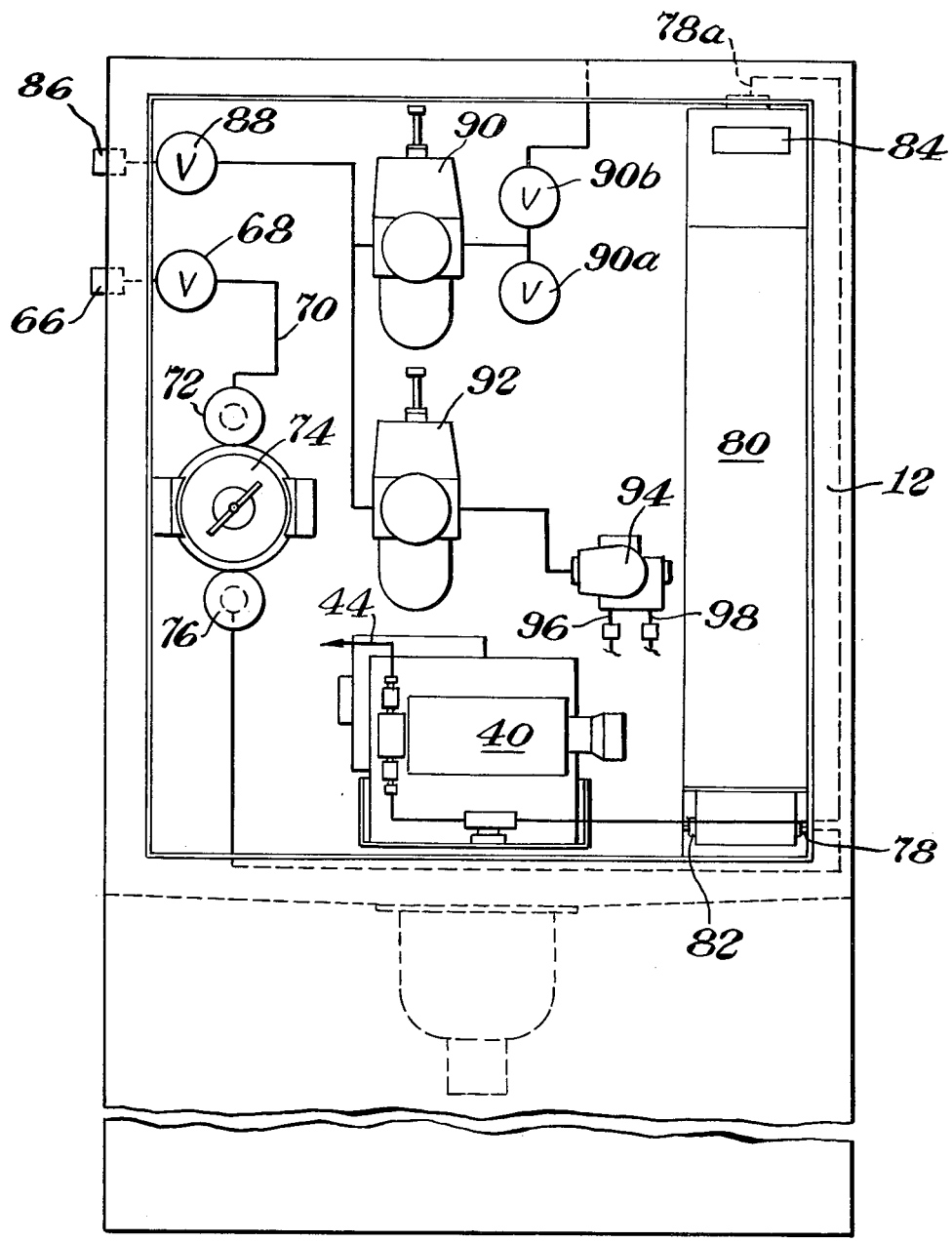
FIG. 2 shows hidden detail of the instrument of FIG. 1 and is also an elevation view.

Referring to FIG. 2, the detail of lower cabinet 12 behind an openable panel 64 includes an inlet fitting 66 for admitting tap water through a shut-off valve 68 connected progressively to an inlet line 70, a line pressure gauge 72, a diaphragm type pressure regulator 74, and a second line pressure gauge 76. The tap water is supplied to the inlet 78 of a water purifying column assembly 80, equipped with a bottom drain 82 and a conductivity meter 84 (the column assembly preferably a Code No. D0800B equpped with a Code No. D0803 cartridge, from Barnstead Co., Boston). The column outlet 78(a) is connected to injection valve 26 through metering pump 40, as described.

An air inlet fitting and line 86 also in the lower cabinet, communicates through a pneumatic shut-off valve 88 with a pair of air pressure regulators 90, 92 of conventional design and connected in parallel. The regulator 90, through needle valve-controlled outleads 90(a), 90(b) purges both the lower and upper cabinet spaces, respectively, with the corrosion inhibiting clean air whereas regulator 92 supplies air to a 4-way solenoid valve 94. The solenoid valve by means of connectors 96, 98 pilots the pneumatic actuators of automatic injection valve 26.

Referring to FIG. 1, the upper cabinet 14 houses a viewed panel 100. Conductivity meters 102, 104 mounted in panel 100 monitor the response of conductivity cells 54, 60, respectively, converting the conductimetric response of the cells to an analog D.C. voltage output. The viewed panel in addition mounts a pair of solid state time delay relays 106, 108 (preferably Type 328 A 200 Q10XX relays from Newark Electronics, Detroit), which provide a variable injection cycle to actuate the injection of the sample and to reset the peak picker circuits, as will be described hereinafter. A read-out analog voltage meter 110 displays the differential output of the dual peak picker circuits of the circuitry described below.

Figure 3:
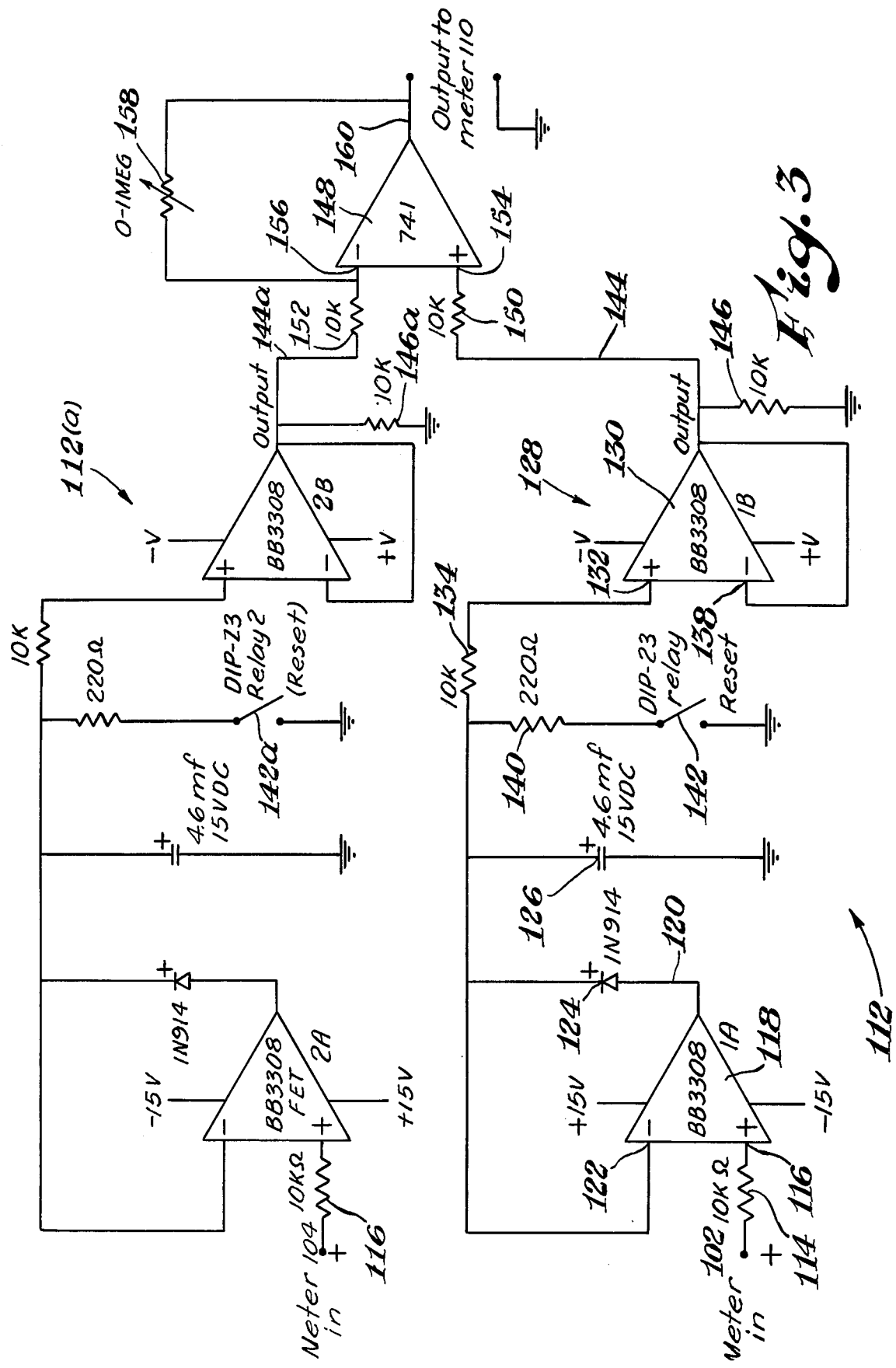
FIG. 3 is a circuit diagram of certain of the electronics of the instrument.

The electronic circuitry comprises dual (identical) peak picker circuits 112, 112(a), shown in FIG. 3, and which receive the analog D.C. output of meters 102, 104, respectively. The circuit 112 is described, and the circuit 112(a) is identified by like reference numerals, but with the added suffix "a".

Circuit 112 includes a resistor 114 that leads into a FET input operational amplifier 118 (preferably a product code No. BB 3308 from Burr-Brown Research Corp., Tucson, Ariz.), with a ±15 D.C. volt power supply (not shown) and preferably an Acopian Model D-15-15A. The output 120 of amplifier 118 is connected to its inverting input 122 through a diode 124. A capacitor 126 maintains a voltage value equal to the most positive value attained on the non-inverting input 116. The information of the capacitor distinguishes the peak voltage of the output signal from conductivity meter 102 for each sample reading. This information is processed and detected by a unity gain buffer amplifier circuit 128. The unity gain buffer amplifier circuit comprises a second FET operational amplifier 130 (preferably also a type BB 3308). Capacitor 126 is connected to the non-inverting input 132 of amplifier 130, through a resistor 134, and the output of amplifier 130 is directly connected to the inverting input 138. The capacitor is reset by a shunted resistor 140 and switch 142 in series.

The output 144, 144(a) of each peak picker circuit 112, 112(a) is connected to ground through a load resistor 146, 146(a), respectively, to stabilize the output from drift. The outputs 144, 144(a) are fed into an operational amplifier 148 (preferably a type 741), through resistors 150, 152, respectively. Circuit 112 is attached to the non-inverting input 154 of amplifier 148, and circuit 112(a) is attached to the inverting input 156. A variable resistor 158 connected between output 160 and inverting input 156 of amplifier 148 thus produces a differential amplifier that amplifies the differential voltage between outputs 144, 144(a). The difference is displayed on read-out panel meter 110.

Instrument Calibration

As a part of the instrument calibration, a standard is prepared of the salt constituent, omitting the base or acid of interest. The calibration standard is injected manually via a syringe into port 22 of selector valve 16. Conductivity meter 104 is adjusted so that the final read-out on voltage meter 110 is zero, after complete sample analysis. Since the derivative acid or base of the salt constituent is usually more responsive, the step will normally require a reduction of sensitivity of the second conductivity meter 104 relative to meter 102. A calibration curve is also prepared by means of injecting a series of acid/salt or base/salt standards of varying concentrations over the range of interest. The calibrated instrument is then prepared for use in the mode described below.

Operation

The sample stream is admitted continuously by-passing through injection valve 26 and on to waste sump 46. Simultaneously, tap water is admitted continuously and purified in column 80, and monitored for ionic purity via meter 84. The resulting purified eluent stream is advanced by pump 40, at a constant rate through the injection valve, carrier loop 28, carrier/sample outlet 36, line 50 and, hence, onto derivatization column 58, and eventually to waste sump 46. Timer 108 establishes the over-all cycle time, and is dialable. Timer 106, also dialable, determines the duration of injection and resets the peak picker circuits through switches 142, 142(a). Following this pattern, timer 106 signals injection valve 26 to inject a sample aliquot into the carrier or eluent stream. At the simultaneous moment, timer 106 activates relays (not shown and preferably Magnecraft No. W172 DIP-23 from Newark), to close switches 142 and 142(a), thereby resetting circuits 112, 112(a) for the analysis of the current sample.

The injected sample first passes through the diffuser column 52 typically diluting the sample concentration (in an approximate gaussion distribution) approximately 80 times at the peak maxima. The sample then passes to the first conductivity cell 54. The reading from the cell 54, (a non-displayed reading indicative of total ionic content) is inputed to circuit 112, through conductivity meter 102. The signal from the meter is held at a maximum positive value by the capacitive voltage storage of peak picker circuit 112. Thus, the information is stored (memorized by the peak picker circuit), and outputed to line 144.

The sample is then passed to the derivatizing column. Assuming a base sample, the base cations are exchanged at the active exchange sites for hydrogen (hydronium) ions, thus being captured and removed from the effluent of the derivatizing column, and the hydroxide ions are converted to $H_2O$ thus blending into the deionized eluent stream. The salt is correspondingly converted to its acid derivative and the salt cations are captured at the column's active ion-exchange sites.

The ion-exchange effluent is passed directly to the second conductivity cell 60, and the information is outputed through meter 104 to peak picker circuit 112(a). The peak picker capacity storage records the maximum positive voltage input value which is outputed to line 144(a). The differential amplifier circuit, through meter 110 displays the differential value of the peak picker outputs from which value the species concentration may thus be predicted. Timer 108 in course cycles out, resetting timer 106. Timer 106 admits the next current sample into the eluent stream and the succeeding sample is analyzed automatically.

Figure 4:
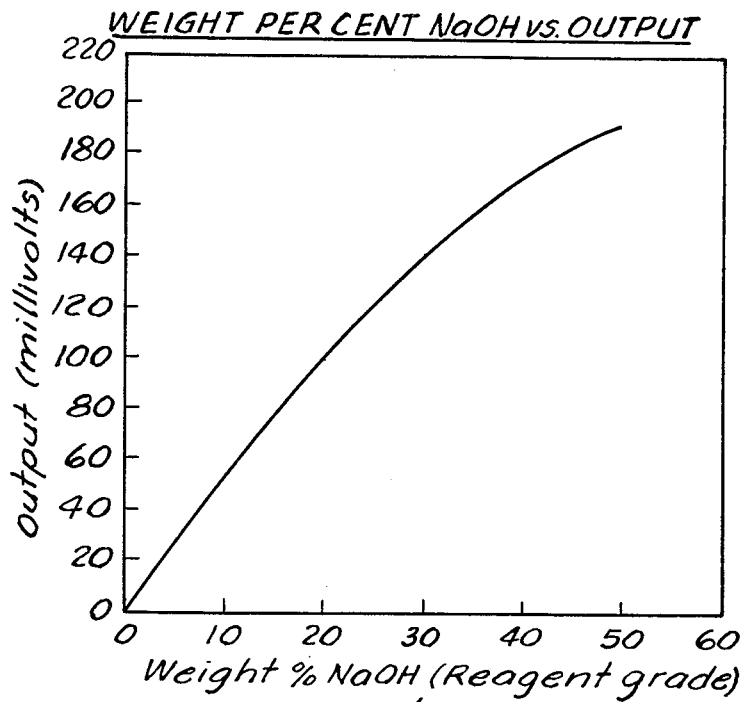
FIGS. 4–5 reproduce a typical calibration curve, and a hard copy strip chart developed using the inventive technique.

FIG. 4 is a plot of a typical calibration curve developed using a series of NaOH standards. Injected standards range up to the 50 percent concentration level and generally the described analytical technique is considered useful up to the solubility limits of the acid or base sample constituents. Linearity, while not absolute, hence does not show loss of sensitivity (i.e., excessive curve flattening). It may also be observed that for a typical process application wherein concentration ranges from 0–20 percent, errors as might be introduced in assuming linearity would not be great. Thus, it is apparent that applications exist where the concentration may be directly reported by the instrument by calibrating at a single point only. Thus response curve linearization electronics or their equivalent are not necessarily required in the practice of the technique of the invention.

Figure 5:
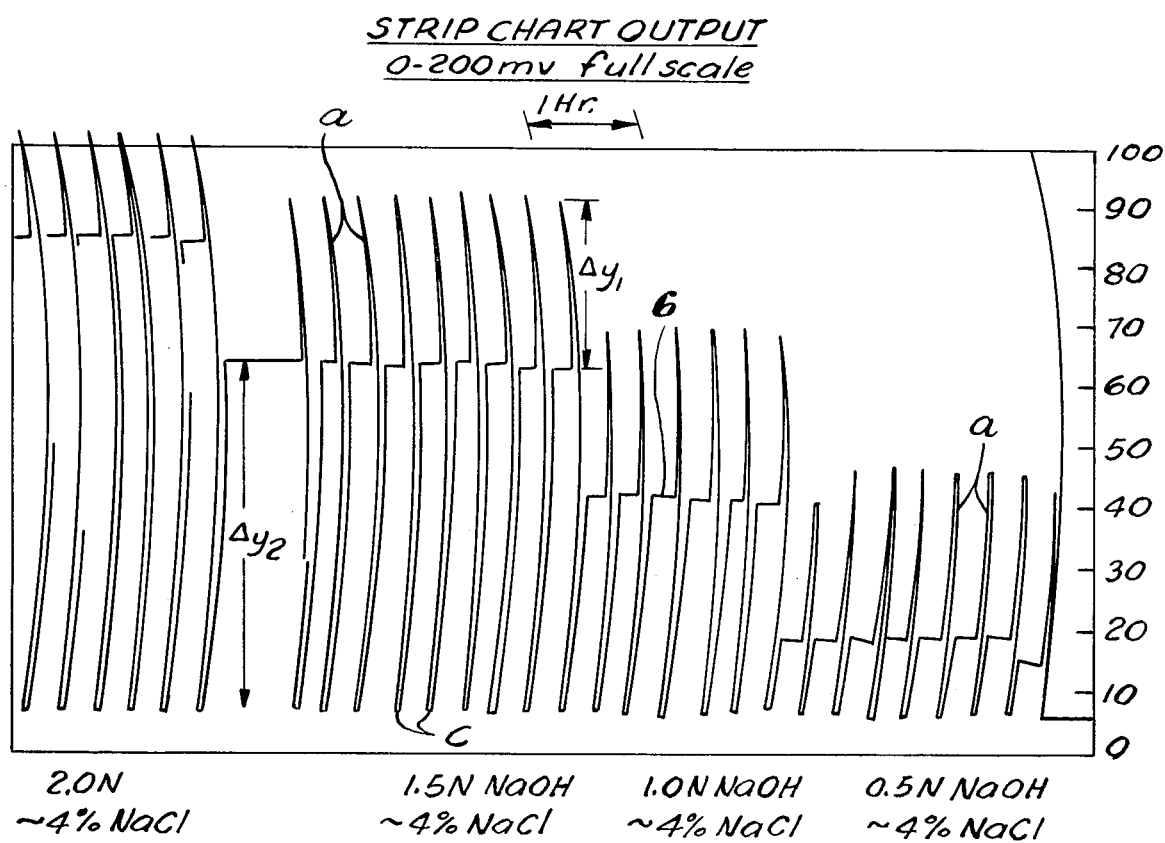

Also, in the usual mode, the instrument may be monitored by suitable hard copy chart recorders to produce strip chart output data forms as generally illustrated by FIG. 5. The experiment uses the following conditions:
  Eluent: Deionized water
  Flow Rate: 84 ml/hour
  Injector Volume: 3.8 μl
  Injection Frequency: 18 min.
  Diffuser Column: 9×250 mm glass column packed with Rohm & Haas XAD-2 resin packing, 80–120 mesh
  Ion-Exchange Column: 9×250 mm glass column packed with Bio-Rad 50WX16, 200–400 mesh in the hydrogen ion form
  Detectors: Model BM-2 conductivity meters from Modern Metalcraft, Midland, Michigan with 2 μl Wescan Model No. 219-200 flow through conductivity cells The data of FIG. 5 is generated using the denoted caustic-salt standards (reagent grade) admitted by the syringe-loaded injection valve technique, which explains the cause of the slight discrepancy indicated by the first peak of the lower right of the chart (caused by insufficient initial flushing of the loop). The base line (c) indicates that differential output resulting from the peak picker reset at the injection time zero. The salt spike or (a) represents the maximum conductivity value reported during sample elution through cell 54, and hence represents combined salt and base response. The reduction to plateau (b) is the consequence of the salt derivative peak elution through cell 60, and hence the valve $\Delta Y_2$ (i.e., total ionic less the salt derivative response) may be used to estimate the base concentration. By the same token, the value $\Delta Y_1$ is proportionately related to the salt concentration, and thus predicative thereof. Similarly, in the case of a mixture of bases and salts or acids and salts, the technique described would, by the same procedure and data, predict total acid or total base (and total salt) concentration.

The experiment of FIG. 5 is repeated using a series of reagent grade NaOH reagent standards in increments from about 0.5 N–2.0 N, omitting the salt constituent. Similar results are observed except without a detectable salt spike (a) in the strip chart output. The absence of an apparent salt spike thus confirms that essentially no detectable caustic derivative, or caustic, or column residue interferences elute from the ion-exchange means. Hence, essentially the total caustic content of the sample is successfully derivatized to water using the preferred and recommended ion-exchange resin, supra.

Analysis of reagent grade HCl samples (no salt constituent) under exactly duplicative conditions to the FIG. 5 experiment, supra, demonstrates no detectable unreacted acid elution using AG1X10 ion-exchange resin, 200–400 mesh, converted to the OH⁻ form by washing with caustic. The experiment thus demonstrates excellent suitability of purpose of this ion-exchange resin for acid analysis. Less suitable results, with some unreacted acid passing through the ion-exchange, is achieved under exactly duplicative conditions, except using AG1X8 resin, 20–50 mesh, from Bio-Rad, available commercially in the OH⁻ ion form. The results are attributed principally to improper mesh size, and would suggest derivatization column size modifications, or most preferably, the recommended use of the AG1X10 resin, 200–400 mesh, for acid/salt analysis under the mode of the invention.

What is claimed is:

1. The analytical method of assaying for acid species concentration in an acid/salt sample matrix by the steps comprising injecting a sample into an aqueous carrier stream, analyzing the sample to obtain a response proportionate to the acid plus salt concentration, derivatizing the acid species to water and the salt to a hydroxide derivative, said derivatization step being carried out in a strong base ion-exchange means in the hydroxide ion form, and wherein the step is characterized by the capture of substantially all of the sample anions at the active ion-exchange sites, and the substitution of a substantially equivalent amount of hydroxide ions, eluting the sample with an aqueous eluent, analyzing the effluent to obtain a response proportionate to the salt concentration, and comparing the thusly taken responses to estimate the acid species concentration.

2. The method of claim 1 wherein said injection and elution step employ the carrier deionized water.

3. The method of claim 1 wherein said sample contains a mixture of acid species, said method being used to quantitate the total acid concentration of the sample.

4. The method of claim 1 wherein the acid species is characterized by a $pK_a$ of about 2 or less.

5. The method of claim 1, with the additional step of employing the effluent response to predict the salt concentration.

6. The method of claim 5 wherein the sample contains a mixture of salts, said method being used to predict total salt concentration.

7. The method of claim 1 wherein the method employs the steps of conductimetrically determining the response of the sample and effluent, respectively.

8. The method of claim 7 wherein the acid/salt sample is characterized by about 90% or greater ionic dissociation in the carrier stream at the location of the first conductimetric analysis step, said 90% ionic dissociation referring to the area of maximum concentration of the sample in the carrier stream.

9. The method of claim 8 wherein said sample is injected into a flowing carrier stream, and including the step prior to said first conductimetric analysis step, of diffusing the sample to produce a generally gaussion distribution of the sample in the carrier stream.

10. The method of claim 9 using a flow-through conductivity detector to determine the response of said sample and effluent, respectively.

11. The method of claim 10 wherein the maximum response value of the sample is compared with the maximum response value of the effluent, and the differential used to predict acid species concentration.

12. The analytical method of assaying for base species concentration in a base/salt sample matrix by the steps comprising injecting a sample into an aqueous carrier stream, analyzing the sample to obtain a response proportionate to base plus salt concentration, derivatizing the base species to water and the salt to an acid derivative, said derivatization step being carried out in a strong ion-exchange means in the hydrogen ion form, and wherein the step is characterized by the capture of substantially all of the sample cations at the active ion-exchange sites, and the substitution of a generally equivalent amount of hydrogen ions, eluting the sample with an aqueous eluent, analyzing the effluent to obtain a response proportionate to the salt concentration, and comparing the thusly taken responses to estimate the base species concentration.

13. The method of claim 12 wherein said sample contains a mixture of base species, said method being used to quantitate the total base concentration of the sample.

14. The method of claim 12 wherein the base species is characterized by a $pK_b$ of about 2 or less.

15. The method of claim 12, with the additional step of employing the effluent response to predict the salt concentration.

16. The method of claim 15 wherein the sample contains a mixture of salts, said method being used to predict total salt concentration.

17. The method of claim 12 wherein said injection and elution step employ the carrier deionized water.

18. The method of claim 17 wherein the method employs the steps of conductimetrically determining the response of the sample and effluent, respectively.

19. The method of claim 18 wherein the base/salt sample is characterized by about 90% or greater ionic dissociation in the carrier stream at the location of the first conductimetric analysis step, said 90% ionic dissociation referring to the area of maximum concentration of the sample in the carrier stream.

20. The method of claim 19 wherein said sample is injected into a flowing carrier stream, including the step prior to said first conductimetric analysis step, of diffusing the sample to produce a generally gaussion distribution of the sample in the carrier stream.

21. The method of claim 19 using a flow-through conductivity detector to determine the response of said sample and effluent, respectively.

22. The method of claim 21 wherein the maximum response value of the sample is compared with the maximum response value of the effluent, and the differential used to predict base species concentration.

23. The analytical method of assaying for salt species concentration in an acid/salt or base/salt sample matrix comprising injecting a sample into an aqueous carrier stream, derivatizing the base or acid interference to water, and the salt to either an acid or hydroxide derivative, said derivatization step being carried out in an ion-exchange means in the strong base/hydroxide ion form for quantitating salt in an acid/salt sample matrix, and in the strong acid/hydrogen ion form for quantitating salt in a base/salt sample matrix, and wherein the step is characterized by the capture of substantially all of the sample anions, or alternately, substantially all of the sample cations at the active ion-exchange sites, eluting the sample with an aqueous eluent, analyzing the effluent to obtain a response proportionate to the salt concentration, and deducing from said response the salt species concentration.

24. The method of claim 23 wherein said injection and elution step employ the carrier deionized water.

25. The method of claim 24 wherein the sample contains a mixture of salts, said method being used to predict total salt concentration.

26. The method of claim 24 wherein the method employs the step of conductimetrically determining the response of the effluent.

27. The method of claim 26 using a flow-through conductivity detector to determine the conductimetric response of said effluent.

28. The method of claim 26 wherein the acid or base species is characterized by a $pK_a$ or $pK_b$, as applies, of about 2 or less.

* * * * *

UNITED STATES PATENT AND TRADEMARK OFFICE
CERTIFICATE OF CORRECTION

PATENT NO. : 4,199,323
DATED : April 22, 1980
INVENTOR(S) : Theodore E. Miller, Jr. and Timothy S. Stevens It is certified that error appears in the above-identified patent and that said Letters Patent are hereby corrected as shown below:

On the cover page, under U. S. Patent Documents, delete "2,920,398" and insert --3,920,398--.

Col. 4, line 59, delete "equpped" and insert --equipped--.

Col. 5, line 35, delete the word "of" and insert --on--.

Col. 6, line 38, delete the word "the" and insert --this--.

Col. 7, line 35, delete the word "that" and insert --the-- after the word "indicates".

Col. 8, line 68, insert the word --acid-- after the word "strong".

Signed and Sealed this

Twelfth Day of August 1980

[SEAL]

Attest:

SIDNEY A. DIAMOND

Attesting Officer　　Commissioner of Patents and Trademarks